United States Patent [19]

Moskowitz

[11] Patent Number: 5,767,117
[45] Date of Patent: Jun. 16, 1998

[54] METHOD FOR TREATING VASCULAR HEADACHES

[75] Inventor: Michael A. Moskowitz, Belmont, Mass.

[73] Assignee: The General Hospital Corporation, Boston, Mass.

[21] Appl. No.: 342,090

[22] Filed: Nov. 18, 1994

[51] Int. Cl.$^6$ .......................... A61K 31/44; A61K 31/505; A61K 31/55

[52] U.S. Cl. .......................... 514/219; 514/220; 514/221; 514/258; 514/292; 514/300

[58] Field of Search .......................... 514/300, 219, 514/220, 221, 258, 292

[56] References Cited

U.S. PATENT DOCUMENTS 5,120,723  6/1992  Gee et al. .......................... 514/176

OTHER PUBLICATIONS

Moskowitz, M. et al., Sumatriptan: A Receptor–Targeted Treatment for Migraine; Annu. Rev. Med. 1993; 44:145–154.
Serensen, K.V.; Valproate: A New Drug in Migraine Prophylaxis; Acta Neurol Scand; 1988; 78:346–348.
Haefely, J. et al., Novel Anxiolytics that Act as Partial Agonists at Benzodiazepine Receptors; TiPS; Nov. 1990; 11:452–456.
Sieghart, W., GABA A Receptors: Ligand–gated Cl–ion Channels Modulated by Multiple Drug–Binding Sites; TiPS; Dec. 1992; 13:446–450.
Guisti, L. et al., Sex Steroid Hormones and GABA A Receptor Complex Modulation; GABAergic Syaptic Transmission; 1992; 133–141.
Jussofie, A.; Brain Area Specific Differences in the Effects of Neuroactive Steroids on the GABA A Receptor Complexes Following Acute Treatment with Anaesthetically Active Steroids; Acta Endo. 1993; 129: 480–485.
Beckham, J. et al., The Relationship of Ovarian Steroids, Headache Activity and Menstrual Distress: A Pilot Study with Female Migraineurs; Headache 1992; 32:292–297.
Moskowitz, M.; Neurovascular and Molecular Mechanisms in Migraine Headaches; Cerebrovascular and Brain Metabolism Reviews; 5:159–177; 1993.
Moskowitz, M. Neurogenic Versus Vascular Mechanisms of Sumatriptan and Ergot Alkaloids in Migraine; Trends in Pharm. Sciences; Aug. 1992; 13:307–311.
Hering, R. et al., Sodium Valproate in the Treatment of Cluster Headace: An Open Clinical Trial; Cephalalgia 1989; 9:195–198.
Sodium Valproate in the Prophylactic Treatment of Migraine: A Double–Blind Study versus Placebo; Cephalalgia 1992; 12:81–84.
Mathew, N.; Valproate in the Treatment of Persistent Chronic Daily Headache. An Open Study; Headache 1991; 31:71–74.
Jones, M. et al.; Effect of Treatment with Sodium Valproate and Diazepam on Plasma Corticotropin in Nelson's Syndrome; the Lancet, May 30, 1991; 1179–1181.
Frye, C. et al., Progesterone Metabolites, Effective in the GABA A Receptor Complex, Attenuate Pain Sensitivity in Rats; Brain Research 643 (1994) 194–203.
Serensen, K.V.; Valproate: A New Drug in Migraine Prophylaxis; Acta Neurol. Scand., 1988:78:346–348.
Hoke, J. et al.; Pharmacokinetics of Vigabatrin Following Single and Multiple Oral Doses in Normal Volunteers; J. Clin. Pharmac. 1993:33:458–462.
Browne, T.R. et al.; Vigabatrin for Refractory Complex Partial Seizures: Multicenter Single–Blind Study with Long–term Follow–up; Neurology 1987:37:184–189.
Ring, H.A. et al.; Vigabatrin: Rational treatment for Chronic Epilepsy; J. Neurology, Neurosurgery and Psych.; 1990;53:1051–55.
Kalviainen, R. et al.; Place of Newer Antiepileptic Drugs in the Treatment of Epilepsy; Drugs 46(6):1009–1024, 1993.
Snyder, S.; Drug and Neurotransmitter Receptors; New Perspective with Clinical Relevance; JAMA, Jun. 2, 1989 261:3126–3129.
Schove, L.T., Bioorganic & Medicinal Chemistry, 2(10):1029–1049 (1994).
TenBrink, R.E., J. Med. Chem., 37:758–768 (1994).
Lee, C.M., et al., Neuroscience Letters, 127:237–241 (1991).
Bennett, D.A., et al., Drug Development Research, 4:75–82 (1984).
Martin, J.R., et al., Drug Development Research, 36:141–149 (1995).
Fryer, R.I., et al., Journal of Medicinal Chem., 36:1669–1673 (1993).
Hollinshead, S.P., et al., J. Med. Chem., 33:1062–1069 (1990).
Marder, M., et al., Biochemical and Biophysical Research Communication, 223:384–389 (1996).
Guerrini, G., et al., Eur. J. Med. Chem. (1996) 31, 259–272.

Primary Examiner—Phyllis G. Spivack
Attorney, Agent, or Firm—Wolf, Greenfield & Sacks, P.C.

[57] ABSTRACT

The present invention provides methods for treating migraine headache. The methods useful according to the invention involve the treatment of patients who experience symptoms of migraine headache with compounds that directly or indirectly activate GABA$_A$ receptors.

12 Claims, 5 Drawing Sheets

METHOD FOR TREATING VASCULAR HEADACHES

This invention was made with Government support under Contract # NS21558 awarded by the National Institutes of Health. The Government has certain rights in this invention.

BACKGROUND

Migraine headache ("migraine") is a common disorder, believed to afflict 20 to 30 percent of the population at large. In migraine patients, throbbing head pain occurs periodically. The pain often is associated with symptoms such as nausea, vomiting and impaired vision. Migraine is a serious clinical disorder requiring medical treatment.

The biochemical mechanisms underlying migraine are uncertain. The predominate belief expressed in the literature for many years was that vasodilation of extracranial vessels causes migraine. Treatment efforts, therefore, were aimed at methods of causing vasoconstriction. More recently, evidence has shown that activation of prejunctional 5-HT$_1$ heteroreceptors on primary afferent trigeminovascular fibers, by drugs such as ergot alkaloids and sumatriptan, alleviate migraine pain, suggesting a neuronal pathogenesis as opposed to a vascular one. Trigeminovascular fibers innervate meningeal blood vessels The interaction of these compounds with the 5-HT$_1$ receptor is very specific. These compounds do not interact with other 5-HT receptors, norepinephrine receptors, glutamate receptors or GABA (gamma-aminobutyric acid) receeptors (Moskowitz et. al., Annu. Rev. Med. 44:145-54 (1993)).

Several other studies suggest that a neuronal mechanism is involved in migraine. Clinical studies have reported the usefulness of valproic acid (2-propylpentanoic acid) for the prophylactic treatment of migraine (Herring & Kuritzky 1992, Jensen et al. 1994), chronic daily headache (Mathew & Ali 1991) and for the treatment of cluster headache (Herring & Kuritzky 1989). Valproic acid, commonly used for the treatment of epilepsy, is a GABA transminase inhibitor (Godin et al. 1969) and an activator of glutamic acid decarboxylase (Loscher 1981). Following its administration, GABA levels increase. It was postulated that sodium valproate could be exerting a GABA-mimetic effect by acting on "GABA receptors, including those on the dorsal raphe nuclei, resulting in a decreased firing rate of the seratonergic neurons with a vasodilating effect" and therefore preventing migraine by inhibiting vasodilation. (Jensen, R., et al., Neurology (1994)44:647-651). It however has never been established that sodium valproate mediates its effect via GABA receptors, although the prevailing theory remains that vasodilation is central to migraine.

The above studies as well as others have resulted in the development of several therapeutic approaches for treating migraine; no one mechanism has been identified yet which appears to be responsible for migraine. Drug treatments for migraine include propanolol, methysergide, tricyclic antidepressants, aspirin like-drugs, ergotamine, ergot alkaloids, valproate and sumatriptan. None of the drugs tested thus far have been completely effective or free of side effects. Some side effects result from administering the drug in such high doses that toxicity rises to unacceptable levels. A real need exists to develop a class of drugs which are effective in treating migraine but do not cause significant side effects.

An object of the invention is to provide classes of compounds that are effective for treating migraine.

Another object of the invention is to provide compounds for treating migraine, which have medically acceptable levels of side effects.

Another object of the invention is to identify a biological pathway involved in migraine and to identify drugs that act on this pathway to inhibit, prevent or alleviate migraine.

SUMMARY OF THE INVENTION

The invention involves the discovery that the GABA$_A$ receptor is central to a neurogenic biological pathway of migraine and further involves the provision of methods for acting on this pathway to inhibit, prevent or alleviate symptoms of migraine.

According to one aspect of the invention a method is provided for treating migraine by administering to a subject in need of such treatment an effective amount of a GABA$_A$ agonist. The preferred GABA$_A$ agonist is THIP.

According to another aspect of the invention a method is provided for treating migraine by administering an effective amount of a GABA uptake inhibitor to a subject in need of such treatment. The preferred GABA uptake inhibitor is tiagabine.

According to another aspect of the invention a method is provided for treating migraine by administering to a subject in need of such treatment an effective amount of a benzodiazepine agonist of the benzodiazepine binding site of GABA$_A$ that modulates GABA$_A$ receptor activity. The preferred benzodiazepine agonists are FG8205, bretazenil, divaplon, alpidem, abecarnil, alprazolam, diazepam, and flunitrazepam.

According to another aspect of the invention a method is provided for treating migraine by administering to a subject in need of such treatment an effective amount of a neurosteroid that modulates GABA$_A$ receptor activity. The preferred neurosteroid is progesterone.

According to another aspect of the invention a method is provided for treating migraine by administering to a subject in need of such treatment an effective amount of a non-valproic acid GABA anti-degradation agent. The preferred non-valproic acid GABA antidegradation agent is vigabatrin.

DETAILED DESCRIPTION OF THE INVENTION

Figure 1:
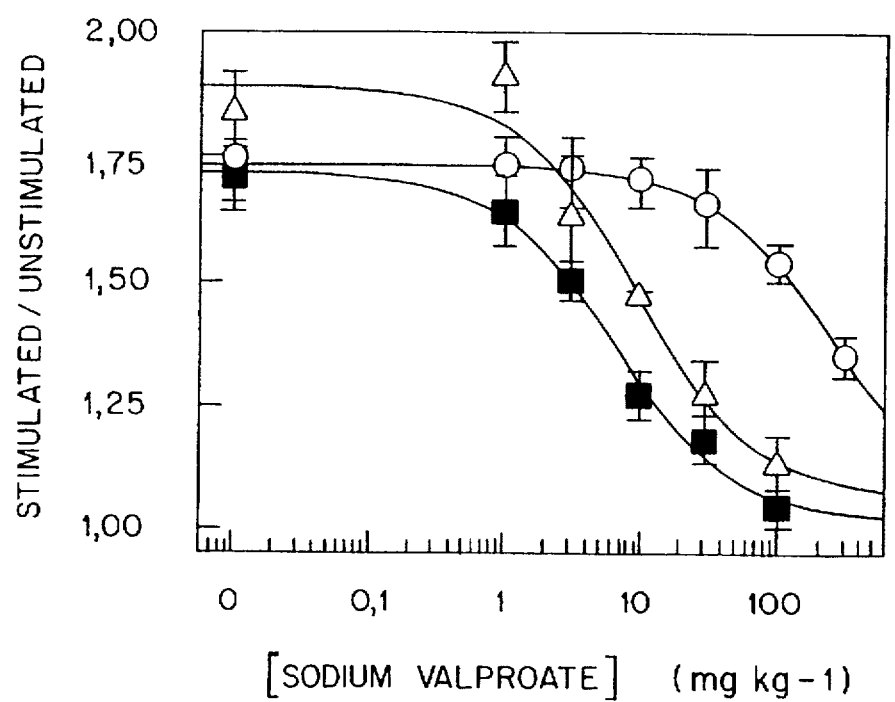
FIG. 1 is a graph depicting the ratio of plasma protein ([$^{125}$I]-BSA) extravasation in stimulated vs. unstimulated animals. The animals were treated with sodium valproate alone ■, bicuculline and sodium valproate, ○, or phaclofec and sodium valproate, △.

GABA, a neurotransmitter, is involved in the inhibition of neurones in the central nervous system as well as in the regulation of a variety of physiological mechanisms in the periphery. The mechanisms underlying the GABA-mediated neurotransmission are complex. Three subpopulations of GABA receptors have been identified to date and may be responsible for some of the complexity seen with GABA mechanisms. The $GABA_A$ receptor, or classic GABA receptor is ubiquitous (Jussofie et. al., Acta Endocrinologica, 1993, 129:480-5). GABAB and GABAc receptors have been less well characterized than the $GABA_A$ receptors.

The present invention utilizes the unexpected finding that classes of compounds can relieve migraine by inhibiting neurogenic inflammation via the $GABA_A$ receptor.

The present invention is useful whenever it is desirable to prevent, inhibit altogether or reduce the symptoms of migraine. The invention thus is useful in the acute treatment of migraine as well as in the prophylactic treatment of migraine. The invention is particularly directed to a patient population never before treated with drugs useful according to the methods of the invention, including patients who are not epileptics undergoing treatment for epileptic seizures, who are not women being treated for premenstrual syndrome or who are not women using oral contraceptive agents. In other words, the treatment preferably is directed to patient populations that otherwise are free of symptoms that call for treatment with any of the drugs useful according to the invention.

Migraine is a disorder which involves complex periodic attacks of vascular headache. Migraine encompasses both classic and common migraine. Vascular headache is generally temporal or unilateral in onset. Migraines are generally familial and often are triggered by factors such as diet, alcohol, chocolate, coffee, exposure to sunlight, exercise, tension, or the use of oral contraceptives, or physiological changes such as occur during the menstrual cycle.

Many mechanisms of action have been proposed for the treatment of migraine headache and a wide variety of drug treatments have been developed based on these mechanisms. None of these drugs has been completely successful in alleviating the symptoms of migraine in the absence of side effects. The present invention involves the unexpected finding that the GABA receptor, and in particular the $GABA_A$ receptor and not the $GABA_B$ or $GABA_C$ receptor, is central to the biochemical pathway of migraine and that modulating this pathway can relieve symptoms of migraine. The pathway may be modulated using $GABA_A$ agonists, GABA uptake inhibitors, benzodiazepines that are GABAergic modulators of $GABA_A$ receptor activity, neurosteroids that are GABAergic modulators of $GABA_A$ receptor activity, and non-valproic acid GABA antidegradation agents.

At least two tests can be used to determine compounds which act via a mechanism that effectively increases $GABA_A$ receptor activity. The tests evaluate the neurogenic inflammation of dura mater occurring as a result of electrical and chemical stimulation of the trigeminovascular system. Neurogenic inflammation is measured by determining the leakage of labeled proteins from the blood into the dura mater. Radiolabeled proteins are injected into an animal, followed by either an electrical stimulation or a chemical stimulation (by substance P) in the presence or absence of a test compound. The amount of radioactive protein which has extravasated from the blood into the dura mater then may be determined. If the test compound is able to inhibit the plasma protein extravasation in a $GABA_A$ specific manner, then it is a compound which is useful in the treatment of migraine. The test compound can be determined easily to be involved in a GABA pathway and in particular to be $GABA_A$ specific (see Examples).

The compounds useful for treating migraine are $GABA_A$ receptor activating compounds. $GABA_A$ receptor activating compounds include $GABA_A$ agonists, GABA uptake inhibitors, benzodiazepines that are GABAergic modulators of $GABA_A$ receptor activity, neurosteroids that are GABAergic modulators of $GABA_A$ receptor activity, and non-valproic acid GABA antidegradation agents.

$GABA_A$ agonists and prodrugs of agonists directly stimulate the $GABA_A$ receptor. The action of these drugs can be inhibited by $GABA_A$ antagonists. As used herein, $GABA_A$ agonists include agonists per se and prodrugs of agonists.

$GABA_A$ agonists useful in treating migraine are muscimol; isoguvacine; THIP: 4,5,6,7-tetrahydroisoxazolo [5,4-c]pyridin-3-ol; IAA: imidazole-4-ethanoic acid; (RS) 2-amino-2-thiazoline-4- ethanoic acid; ZAPA: (z)-3-[(aminoiminomethyl)-thio] prop-2-enoic acid; (1S,3S) TACP: (1S, 3S)-3-aminocyclopentane -1- carboxylic acid; Thio-THIP; Isonipecotic acid; SL75102; dihydromuscimol (S-DHM); DHP4S: 1,2,3,6-tetrahydropyridine-4-sulfonic acid; and P4S: Piperidine-4-suflonic acid. The chemical structures of some of these compounds are presented in Table 1.

TABLE 1

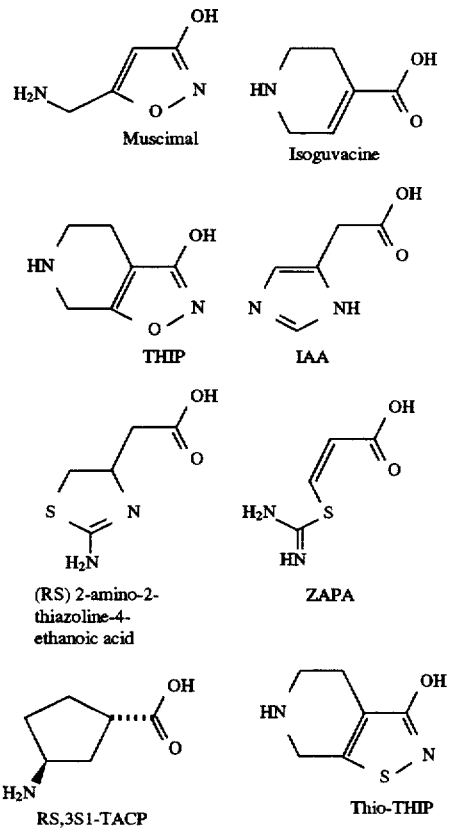

TABLE 1-continued

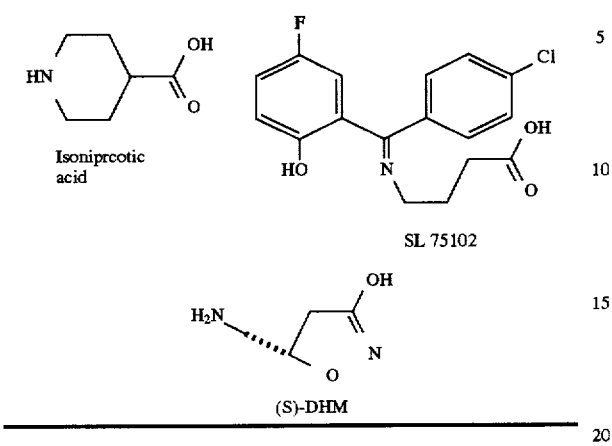

Isonipecotic acid

SL 75102

(S)-DHM

GABA$_A$ receptors are known to possess modulatory sites that bind molecules other than GABA. Such GABA$_A$ receptor modulatory binding sites bind molecules including barbituates, alcohol, benzodiazepines, metabolites of progesterone and other neurosteroids (MacDonald and Olson, 1994). Such molecules, once bound to the GABA$_A$ receptor, allosterically modify the GABA$_A$ binding site and influence receptor activity in an agonistic manner. Thus, such molecules also are useful according to the invention as indirect agonists of GABA$_A$ receptor activity.

Benzodiazepine agonists of the benzodiazepine binding site of GABA$_A$ are compounds that bind to the benzodiazepine binding site of the GABA$_A$ receptor and allosterically modify the receptor in a manner that increases the activity of the GABA$_A$ receptor in the presence of GABA (i.e., they are "GABAergic"). Such compounds and GABA$_A$ modulatory activity are well known to those of ordinary skill in the art. Two types of benzodiazepine receptors exist, central and peripheral. Central receptors are located within the brain and spinal cord. The central benzodiazepine receptor is part of the GABA$_A$ receptor and has a recognition site which is distinct from the GABA$_A$ recognition site. Binding of benzodiazepine to the recognition site modulates the GABA receptor activity in an agonistic manner. Low concentrations of GABA enhance the affinity of benzodiazepines for the receptor and activate the receptor. Different benzodiazepine receptor agonists have different potencies for the central and peripheral receptors. For instance clonazepam is more potent at central than peripheral receptors by a few thousand times. Others, like diazepam, have roughly equal potencies at both.

Benzodiazepine agonists that bind to the GABA$_A$ receptor and are useful in treating migraine include clonazepam, FG8205, bretazenil (Rol66028); divaplon (RU32698); alpidem; abecarnil (ZK11219); alprazolam; diazepam; zolpidem; flunitrazepam; Ro54864: 7-chloro-1,3-dihydro-1-methyl-5-(p-chlorophenyl)-2H-1,4-benzodiazepine-2-one; PK8165: phenyl-2[(piperidinyl-4)-2-ethyl]-4-quinoline; PK9084: phenyl-2[(piperidinyl-3)-2-ethyl]-4-quinoline; and PK11195: 1-(2-chlorophenyl)-N-methyl-N-(1-methyl-propyl)-3-isoquinalinecarboxamide. The chemical structures of some of the compounds are presented in Table 2.

TABLE 2

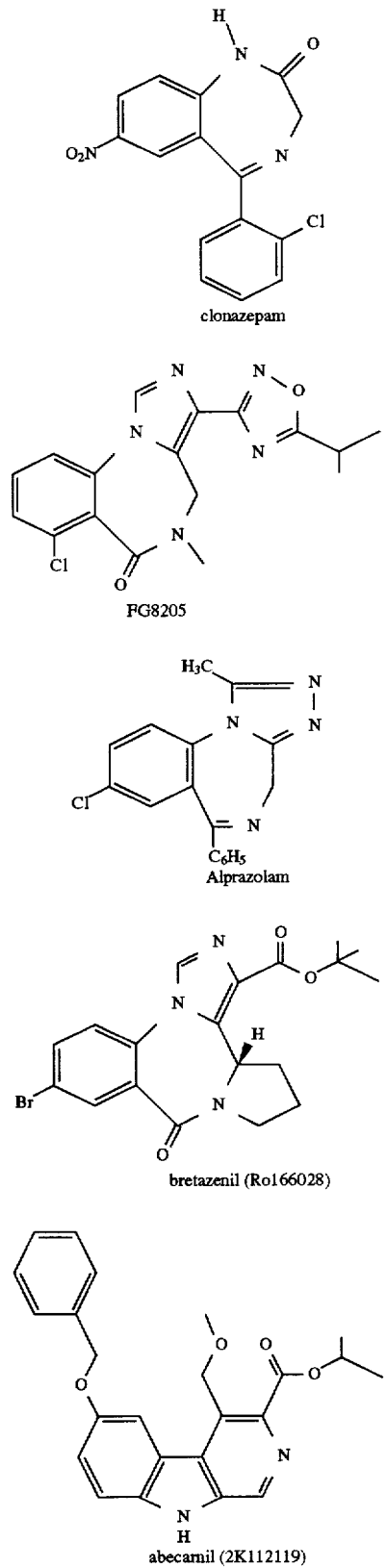

clonazepam

FG8205

Alprazolam bretazenil (Ro166028)

abecarnil (2K112119)

TABLE 2-continued

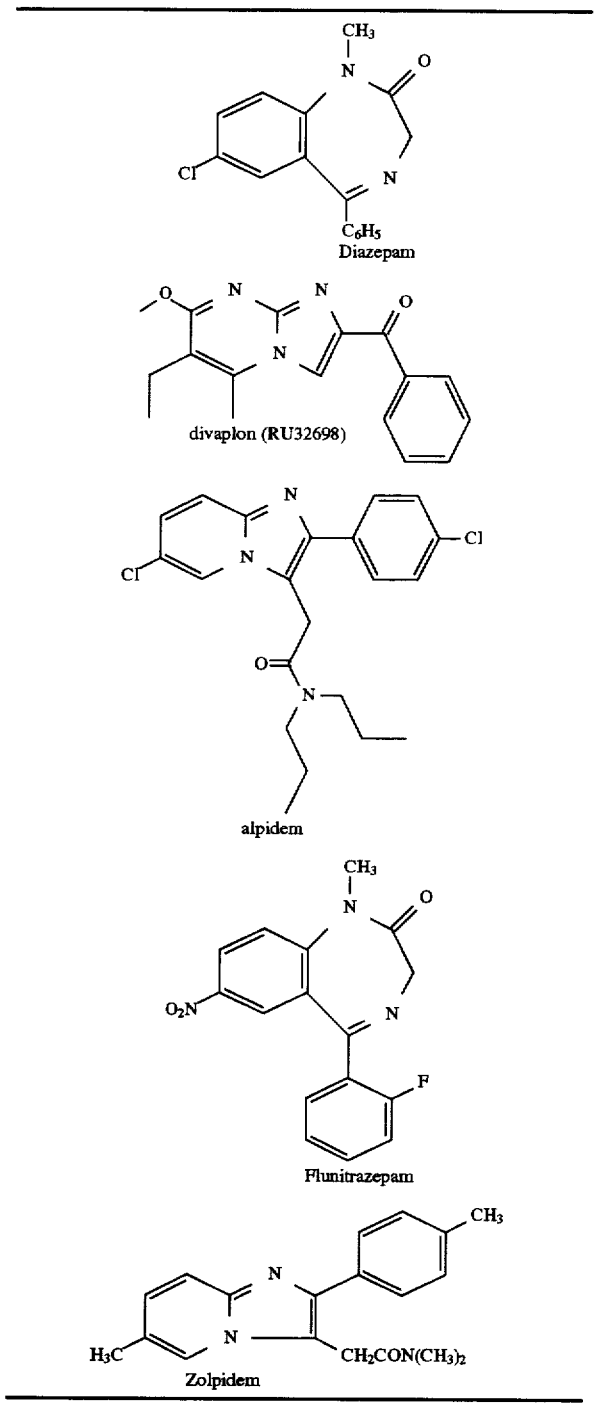

Neurosteroids recognize a different modulatory site on the GABA$_A$ receptor. Binding of these compounds to this recognition site also affects the GABA$_A$ receptor in an agonistic fashion. As used herein, neurosteroids include neurosteroids per se and prodrugs of neurosteroids.

Neurosteroids useful in the invention include progesterone; progeterone metabolites such as allopregnanolone: 5apregnan-3β-DL-20-one; 3α,5α-THP: 3αhydroxy-5αpregnan-20-one; 3ahydroxy-5βpregnan-20-one; and 5apregnan-3α, 20α-diol.

The invention also contemplates the use of compounds that are 'effective' agonists of the GABA$_A$ receptor. By effective agonist it is meant compounds that have the same effect as stimulating the GABA$_A$ receptor, that is drugs that increase the concentration of GABA, thereby resulting in more activation of the GABA$_A$ receptor.

GABA uptake inhibitors and antidegradation agents both function in this manner by increasing the GABA concentration in an area local to the GABA$_A$ receptor. GABA uptake inhibitors are compounds which act upon a recognition site which is responsible for taking up GABA and removing it from the GABA receptor active site thereby increasing the concentration of GABA. GABA uptake inhibitors useful in treating migraine include THPO: 4,5,6,7-tetrahydroisoxazolo [4,5-c]pyridin-3-ol); Nipecotic acid; guvacine; Thio-THPO; SKF89975A; tiagabine: 1-(4,4-bis [3-methyl-2- thienyl)-3-bytenyl]; CI-966: 1-(2-(bis(4-(trifluoromethyl)phenyl) methoxy)ethyl)-1,2,5,6-tetrahydrochloride; and DBP-THPO: 4,4-diphenyl-3-butenyl, 4,5,6,7-tetrahydroisoxazolo [4,5-C] pyridin-3-ol. The chemical structures of some of these compounds are shown in Table 3.

TABLE 3

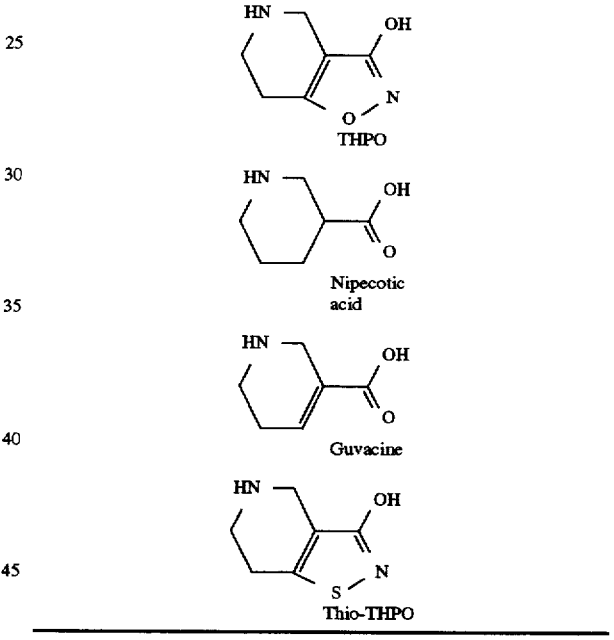

GABA antidegradation agents function by inhibiting the activity of enzymes responsible for the catabolism of GABA. One such enzyme is GABA transaminase. Treatment with GABA antidegradation agents results in decreased catabolism of GABA and thus an increase in available GABA.

The GABA antidegradation agent useful in the invention is vigabatrin: y-vinyl GABA (Sabril, Merrell Dow). Vigabatrin has the following structural formula:

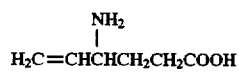

Several of the foregoing compounds have been tested and approved for use in humans for purposes other than the treatment of migraine. These compounds include THIP, tiagabine, FG8205, bretazenil, divaplon, alpidem, abecarnil, alprazolam, diazepam, and flunitrazepam.

In a preferred embodiment of the invention the compound which activates $GABA_A$ receptors is specifically selective for a peripheral receptor. A compound which is specifically selective for a peripheral receptor is one which acts only on a peripheral noncentral receptor. In a further embodiment the compound is a noncentral acting drug. A noncentral acting drug is one that either acts only on noncentral receptors or that does not cross the blood brain barrier and act on central receptors in amounts that result in medically unacceptable side effects.

The invention thus contemplates the use of compounds which increase $GABA_A$ activity but that do not cross the blood brain barrier. Tremor and drowsiness caused by central nervous system actions may appear with treatment involving drugs that cross the blood brain barrier. The data presented in the Example section indicates that valproate inhibits plasma leakage produced by exogenous substance P in intact animals as well as after destruction of unmyelinated C fibers. Based on this data, it appears as though a peripheral GABAA receptor most likely mediates the valproate inhibition of plasma leakage. Therefore, valproate may not need to cross the blood brain barrier in order the reduce the inflammatory response within the meninges. This suggests that brain impermeant GABAergic agents devoid of central side effects will be useful in migraine.

The compounds useful in the invention thus may be modified so that they do not cross the blood brain barrier. Attachment of a Quarternary ammonium group on such compounds introduces a charge on the molecule which renders a previously penetrable compound relatively impenetrable of the blood brain barrier. Other procedures for decreasing the penetrability of the compound into the brain involve increasing the molecular weight or decreasing the lipid partition coefficient. Those of ordinary skill in the art will know other mechanisms for modifying molecules to prevent their passage across the blood brain barrier.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. Such pharmacologically and pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

The compounds useful in the invention may be delivered in a mixture with other anti-migraine drugs including propanolol, methysergide, tricyclic antidepressants, aspirin like-drugs, ergotamine, ergot alkaloids, valproate, sumatriptan, stadol, and $Ca^{++}$ channel blockers.

The formulations of the invention are administered in effective amounts. An effective amount is one sufficient to inhibit plasma protein leakage, thereby effectively decreasing or preventing the resultant head pain of migraine. Effective amounts will depend, of course, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosages are estimated based on the measured inhibition of neurogenic plasma protein leakage in experimental models. Dosages should be sufficient to block neurogenic plasma protein leakage for 90 minutes in cases of acute treatment whereas protein leakage should be inhibited for at least 3 hours when administered chronically. Generally, daily oral prophylactic doses of active compounds will be from about 0.01 milligrams/kg per day to 2000 milligrams/kg per day. It is expected that oral doses in the range of 10 to 500 milligrams/kg, in one or several administrations per day, will yield the desired results. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

A variety of administration routes are available. The particular mode selected will depend of course, upon the particular drug selected, the severity of the migraine state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis. They could, however, be preferred in acute emergency situations. Oral administration will be preferred for prophylactic treatment because of the convenience to the patient as well as the dosing schedule.

The compositions may conveniently be presented in unit dosage form and may be prepared by any of the methods well known in the art of pharmacy. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachettes, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

Use of a long-term sustained release implant may be particularly suitable for prophylactic treatment of migraine. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

EXAMPLES

Materials:

Drugs: [$^{125}$I]-Bovine serum albumin (BSA,; New England Nuclear, Boston, Mass. U.S.A.) was diluted in saline. Substance P (SP), sodium valproate (Sigma Chemicals Inc., St. Louis, Mo., U.S.A.) and muscimol hydrobromide (Research Biochemicals Inc., Natick, Mass., U.S.A.) were dissolved in saline. Capsaicin (Polyscience Inc., Wilmington, Pa., U.S.A.) was dissolved in a solution containing saline-ethanol-Tween 80 (8:1:1). (±)Baclofen, (±)bicuculline and phaclofen (Research Biochemicals Inc., Natick, Mass., U.S.A.) were dissolved in 0.1 N HCl, and the pH was adjusted to 5.0 with a few drops of 0.1 N NAOH. The highest concentration of baclofen (10 mg/kg) was dissolved in 45% 2-hydroxypropyl-cyclodextrin (Research Biochemicals Inc., Natick, Mass., U.S.A.).

Animals: Male Sprague-Dawley rats (200–250 g, Charles River Laboratories, Wilmington, Mass., U.S.A.) were housed under diurnal lighting conditions and allowed food and water ad libitum.

Data Analysis: Data are given as mean±sem. [$^{125}$I]-BSA extravasation is expressed as the ratio of cpm/mg of wet weight (stimulated side)/cpm/mg of wet weight (unstimulated side). Results with substance P are expressed as percent of cpm/mg of tissue in the substance P- versus vehicle-treated animals. ED$_{50}$ value (the dose at which [$^{125}$I]-BSA extravasation was inhibited by 50%) was determined by regression analysis using Grafit (Sigma, St. Louis, Mo., U.S.A.). The Student's t-test was used for statistical analysis (unpaired t-test for comparisons between control and drug-treated groups and paired t-test for comparison between stimulated and unstimulated sides). Two way analysis of variance was used to determine the effects of antagonists on valproate dose/response curve. Probability values (P) of less than 0.05 were considered significant.

EXAMPLE 1

Electrical trigeminal ganglion stimulation and tissue dissection:

Anaesthetised animals (pentobarbitone sodium, 60 mg/kg, i.p.) were placed in a stereotaxic frame (DKI 900, David Kopf Instruments, Tujunga, Calif., U.S.A.) with the incisor bar set at −1.5 mm from the horizontal line, and the calvarium was exposed by a midline incision. The right femoral vein was exposed and [$^{125}$I]-BSA (50 µCi/kg) was injected as a bolus. Symmetrical burr holes of 2 mm in diameter were drilled at 3.7 mm posterior to the bregma and 3.2 mm lateral to the sagittal suture for electrode placement. Bipolar electrodes (50 mm shaft, Rodes Medical Instruments, Woodland Hills, Calif., U.S.A.) were lowered into the trigeminal ganglia to a depth of 9.5 mm from the dura mater overlying the dorsal surface of the brain. The right trigeminal ganglion was stimulated for 5 min (0.6 mA, 5 ms, 5 Hz) (Pulsemaster A300 and Stimulus Isolator A365, World Precision Instruments, San Carlos, Calif., U.S.A.; Oscilloscope V-134, Hitachi Densi, Tokyo, Japan). Immediately after stimulation, the animals were perfused with saline via the left cardiac ventricle for 2 min. at a constant pressure of 100 mmHg in order to remove completely iodinated albumin from the lumen of blood vessels. The skull was then opened, the brain removed and the cranial cavity rinsed with saline. The dura mater was dissected bilaterally and the radioactivity determined on the two sides with a gamma-counter (Micromedic 4/600, Micromedic Systems Inc., Huntsville, Ala., U.S.A.) as previously described (Markowitz et al., 1987).

In preliminary experiments, we determined that sodium valproate exhibited maximum inhibitory effect on the leakage of [$^{125}$I]-BSA within dura mater after electrical trigeminal stimulation when given as a single dose (10 mg/kg, i.p.) 30 min before stimulation; when given 60 min or 120 min before stimulation the drug was without significant effect (data not shown). Therefore, we administered sodium valproate (i.p.), muscimol or baclofen (i.v.) 30 min before electrical trigeminal stimulation and 25 min before [125I]-BSA injection. Bicuculline (0.01 mg/kg) or phaclofen (0.1 mg/kg) were administered 5 min before sodium valproate, muscimol or baclofen treatment. Electrical trigeminal stimulation in the absence of drug treatment results in increased plasma protein extravasation:

Unilateral electrical trigeminal ganglion stimulation increased the leakage of [$^{125}$I]-BSA within the dura mater of rats treated with vehicle from 34.7±3.7 to 59.1±5.7 cpm/mg wet weight (P<0.001, n=4). The ratio between the stimulated and unstimulated sides was 1.71±0.07 and was similar to previously reported values after saline-vehicle administration (Buzzi et al., 1991).

Sodium valproate treatment inhibits plasma protein extravasation:

Sodium valproate (>3 mg/kg; p<0.05; filled squares) dose-dependently decreased plasma protein ([$^{125}$I]-BSA) extravasation in rat dura mater following electrical trigeminal stimulation (0.6 mA, 5 ms, 5 Hz, 5 min) (FIG. 1). The ratio decreased from 1.71±0.07 (vehicle) to 1.50±0.04, 1.27±0.05, 1.18±0.05 and 1.04±0.04 at valproate doses of 3 mg/kg, 10 mg/kg, 30 mg/kg and 100 mg/kg (n=4 per group). The ED$_{50}$ value was 6.6±1.4 mg/kg. Leakage of plasma protein on the unstimulated side did not differ between the treated and untreated groups. Doses of greater than 3 mg/kg decreased extravasation as compared to vehicle (p<0.01). Immediately after stimulation, animals were perfused and dura dissected as described above. Results are expressed as the ratio of the cpm/mg wet weight on the stimulated side to that on the unstimulated side (mean±s.e.mean).

GABA receptor antagonists block sodium valproate inhibition of plasma protein extravasation:

The valproate effect was completely reversed by the GABA$_A$ receptor antagonist bicuculline (0.01 mg/kg; empty circles). Bicuculline (0.01 mg/kg) when administered i.p. 5 min prior to sodium valproate shifted the dose-response curve of sodium valproate by a factor 40 (FIG. 1). Treatment with phaclofen (0.1 mg/kg; empty triangles) shifted the valproate dose-response curve two-fold to the right. The dose-response shift was significant (FIG. 1; p<0.001): in the presence of phaclofen (0.1 mg/kg), valproate EC$_{50}$ value was 13.3±4.8 mg/kg. At the doses used, bicuculline and phaclofen did not by themselves affect the plasma protein extravasation response (data not shown).

Figure 2:
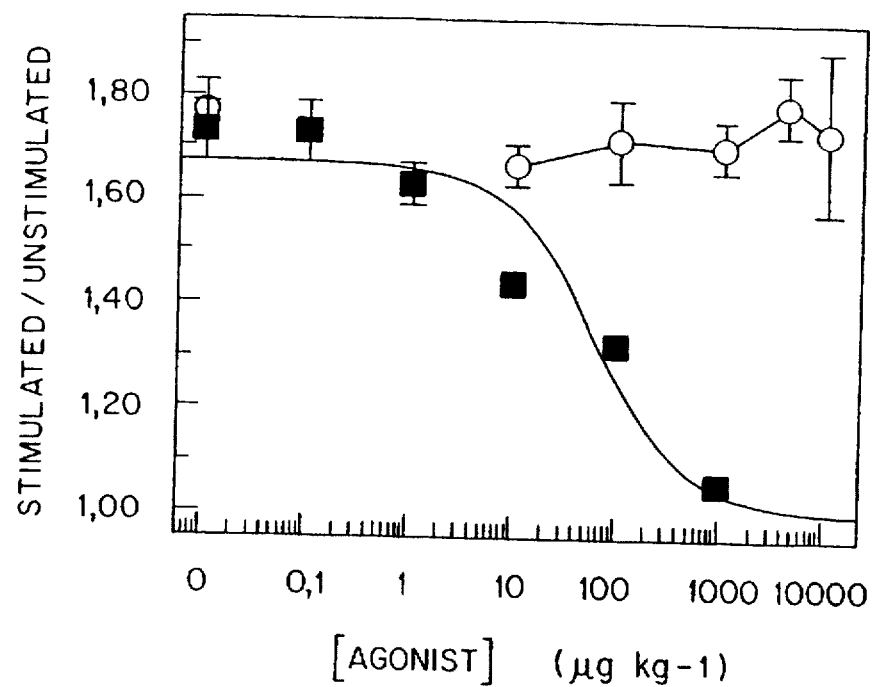
FIG. 2 is a graph depicting the ratio of plasma protein ([$^{125}$I]-BSA) extravasation in stimulated vs. unstimulated animalsN The animals were treated with muscimol■ or baclofen, ○.

Direct GABAA receptor agonists but not GABAB receptor agonists inhibit plasma protein extravasation:

Muscimol (GABAA receptor agonist) or baclofen (GABAB receptor agonist) was administered i.v. 30 minutes prior to electrical trigeminal stimulation and 25 minutes prior to [$^{125}$I]-BSA injection. Muscimol (filled squares) but not baclofen (empty circles) reduced the leakage in dura mater induced by trigeminal stimulation in a dose-dependent manner (FIG. 2). The threshold was 10 µg/kg and leakage ratio was reduced from 1.73±0.06 in vehicle group (n=8) to 1.44±0.03 at the 10 µg/kg concentration (P<0.01, n =7). ED50 was 58±18 µg/kg. Increasing muscimol concentration seemed to yield a shallow dose-response curve (i.e. with a slope <1), but the limited number of concentrations analyzed precluded a more detailed analysis. In a dosage of 1000 µg/kg muscimol caused an almost complete blockade of plasma extravasation (n=5 per group). Baclofen, even at high concentrations (4 mg/kg [n=5]; 10 mg/kg [n=3]), did not affect the plasma protein extravasation following trigeminal electrical stimulation.

Benzodiazepine receptor agonists and neurosteroid metabolites inhibit plasma protein extravasation:

Zolpidem (100 µg/kg), a benzodiazepine receptor agonist, and allopregnanolone (100 µg/kg), a neurosteroid metabolite, were administered i.v. 30 minutes prior to electrical trigeminal stimulation and 25 minutes prior to [$^{125}$I]-BSA injection. Both zolpidem and allopregnanolone reduced the leakage in dura mater induced by trigeminal stimulation (Table 4). Table 4 also provides the results of i.v. administration of sodium valproate (30 mg/kg), sodium valproate (30 mg/kg)+bicuculline (0.01 mg/kg), muscimol (1 mg/kg), and baclofen (10 mg/kg) for comparison. The decrease in plasma extravasation observed with zolpidem and allopregnanolone is similar to that seen with valproate and muscimol.

TABLE 4

| Treatment | Extravasation Ratio (stimulated/unstimulated) Ratio (mean ± s.e.m.) |
| --- | --- |
| Saline | 1.74 ± 0.08 |
| sodium valproate (30 mg/kg) | 1.18 ± 0.0 |
| sodium valproate (30 mg/kg) + Bicuculline (0.01 mg/kg) | 1.65 ± 0.0 |
| Muscimol (1 mg/kg) | 1.06 ± 0.0 |
| Baclofen (10 mg/kg) | 1.74 ± 0.1 |
| Zolpidem (100 µg/kg) | 1.14 ± 0.0 |
| Allopregnanolone (100 µg/kg) | 1.06 ± 0.0 |

EXAMPLE 2

Substance P-Induced Plasma Protein Extravasation:

Substance P administration: Substance P (SP) (1 nmol/kg, i.v.) was administered 5 min after [$^{125}$I]-BSA injection. Animals were perfused transcardially 10 min after SP administration. The dosage of SP was chosen based on previously published data showing that 1 nmol/kg caused plasma protein extravasation in dura mater similar to that following an electrical stimulus (Buzzi & Moskowitz, 1990; Markowitz et al., 1987).

Figure 3:
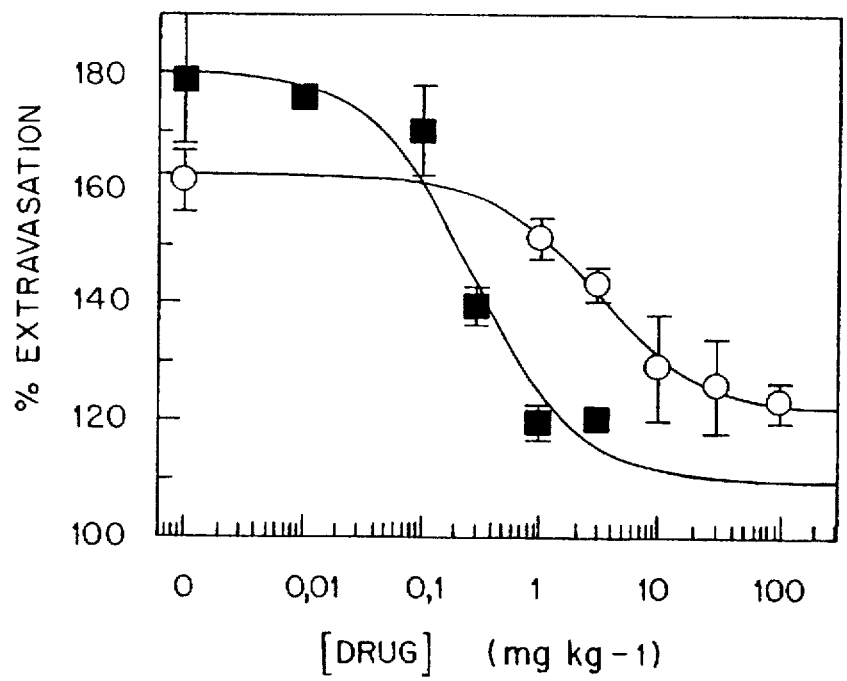
FIG. 3 is a graph depicting the percent plasma protein extravasation inhibited by sodium valproate, ○, or muscimol■, following substance P treatment of animals.

Sodium valproate treatment inhibits SP-induced plasma protein extravasation:

SP increased the amount of iodinated albumin within dura mater by 161±5% (from 71±4 (n=7) to 115±4 cpm/mg; P<0.001, n=7). Sodium valproate 1 (n=4), 3 (n=7), 10 (n=6), 30 (n=5) or 100 (n=3) mg/kg was administered i.p. 30 min before SP injection. Ten minutes after SP injection, animals were perfused and dura dissected as described above. When sodium valproate was administered prior to SP, the SP-induced plasma protein extravasation was decreased in a dose-dependent manner (FIG. 3). At the valproate threshold dose (3 mg/kg) substance P only increased plasma extravasation by 143±3% (P<0.05, n=7). The highest dose tested, 100 mg/kg, was not able to completely reverse the SP effect (123±3%). The ED$_{50}$ for the valproate response was 3.2±0.5 mg/kg. Data are expressed as percent of cpm/mg of tissue in the substance P- (i.e. 0 mg/kg drug) versus vehicle-treated animals (i.e. 100%; n=7).

Direct GABAA receptor agonists inhibit SP-induced plasma protein extravasation:

Muscimol (filled squares) reduced SP-induced plasma protein extravasation in a dose-dependent manner (FIG. 3). The threshold here was 300 µg/kg, which reduced the plasma extravasation from 177±4% to 137±8%. The highest muscimol concentration was not able to completely reverse the SP effect (120±6%). EC$_{50}$ value was 385±190 µg/kg. In contrast to the muscimol dose-response curve in electrically-induced extravasation (FIG. 2), the effect of muscimol on SP-induced extravasation (FIG. 3) was well-fitted with a sigmoid of slope 1.

Figure 4:
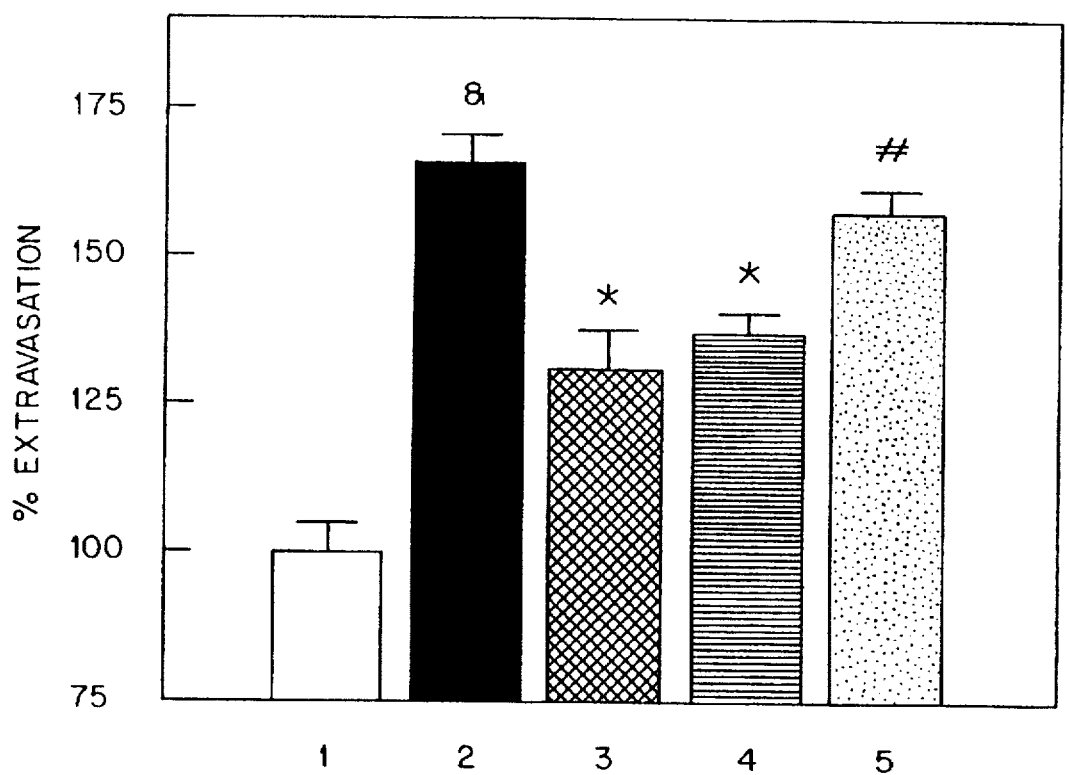
FIG. 4 is a graph depicting the percent plasma protein extravasation induced in vehicle treated (1), 2 substance P treated (2), substance P and sodium valproate treated (3), substance P, sodium valproate and phaclofen treated (4), or substance P, sodium valproate and bicuiculline treated (5) animals.

GABA receptor antagonists block sodium valproate inhibition of SP-induced plasma protein extravasation:

As shown in FIG. 4, pretreatment with bicuculline (0.01 mg/kg, n=3; lightly stippled bar) completely blocks the inhibitory effect of sodium valproate (10 mg/kg) on substance P induced extravasation. In the absence of antagonist, valproate decreased the extravasation ratio to 130±7% (n=9), however when the rats were pretreated with bicuculline the ratio was significantly higher (157±4% P<0.05, n=3). The latter ratio was not significantly different from that obtained when SP was administered alone (p>0.05). Phaclofen (0.1 mg/kg n=3; horizontal hatched bar) did not reverse the effects of sodium valproate. The receptor antagonists were given i.p. 5 min before sodium valproate treatment (10 mg/kg, n=9) and 35 min before SP injection [P<0.001 as compared to vehicle-treated group (open bar; n=9); #P<0.01 as compared to SP alone (n=9; solid bar); #P<0.05 as compared to SP plus valproate group (cross-hatched bar) and no significant difference with the group given SP alone].

EXAMPLE 3

Neonatal capsaicin pretreatment: To destroy unmyelinated C fibers within dura mater, rats were treated with capsaicin (50 mg/kg, s.c. or vehicle for control animals) within the first 48 hr of life as previously described (Jancso et al., 1977). During capsaicin or vehicle injection, animals were kept in a tent containing an aerosol of isoproterenol (0.25 mg/ml for 10 min). After capsaicin or vehicle injection, neonates were returned to their dam. Three weeks later, they were maintained on a diurnal lighting cycle (4 per cage) and allowed to access food and water ad libitum. At time periods beyond 8 weeks, those animals found to be insensitive to the ocular administration of topical capsaicin (wipe test) were studied.

Figure 5:
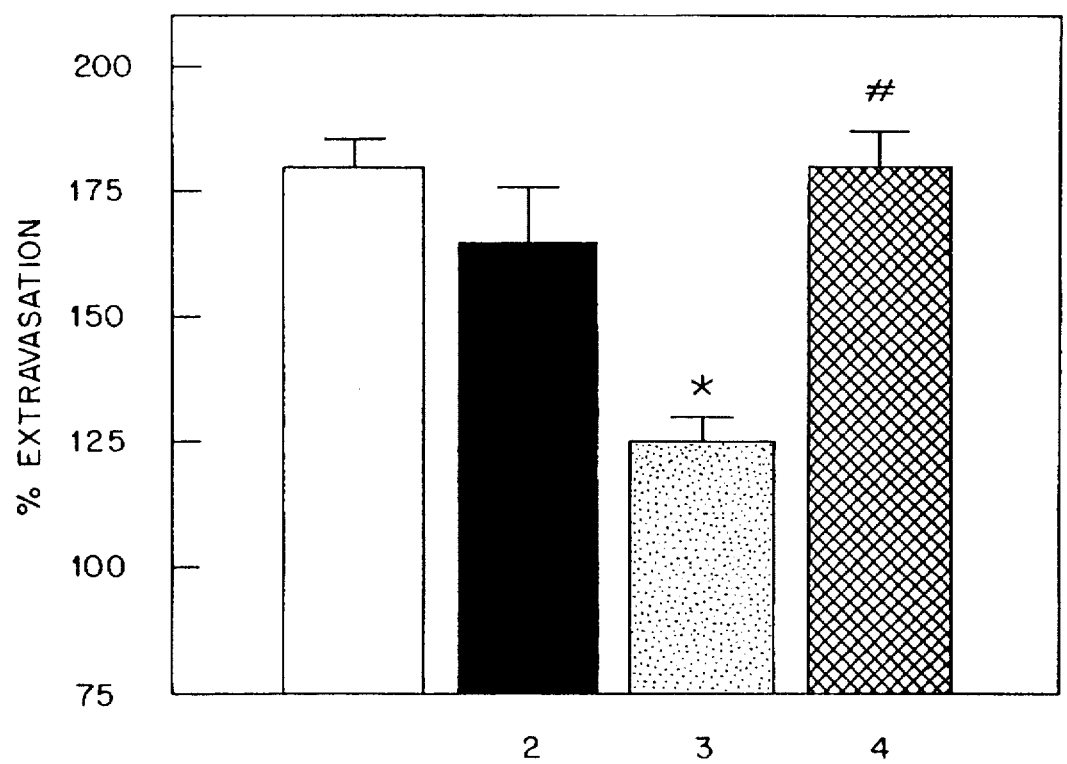
FIG. 5 is a graph depicting the percent plasma protein extravasation induced in substance P treated (1), substance P and sodium valproate (10 mg/kg) treated (2), substance P and sodium valproate (100 mg/kg) treated (3), or substance P, sodium valproate (100 mg/kg) and bicuculline treated (4) animals.

Sodium valproate (solid bar: 10 mg/kg; lightly stippled bar: 100 mg/kg) decreased SP-induced plasma protein extravasation in dura mater of adult rats after capsaicin neonatal treatment. A dose of 100 mg/kg reduced the extravasation from 179±9% (n=6) to 126±6% (n=5). Bicuculline (0.01 mg/kg; cross-hatched bars) reversed the valproate effect when administered i.p. 5 min before sodium valproate pretreatment. * P<0.05 as compared to SP alone (open bar); P<0.05 as compared to valproate (100 mg /kg) treated animals (FIG. 5).

SUMMARY:

Valproate (>3 mg/kg) blocks plasma protein extravasation caused by trigeminal ganglion stimulation or by intravenous substance P. This effect is mimicked by the GABAA receptor agonist muscimol, a structural analogue of GABA, the benzodiazepine receptor agonist, zolpidem, the neurosteroid, allopregnanolone and reversed by the competitive $GABA_A$ receptor antagonist bicuculline. The $GABA_B$ receptor agonist baclofen has no effect on plasma protein extravasation, even at high concentration (4 and 10 mg/kg). Plasma protein extravasation in this study was measured using a standard protocol including pentobarbital anesthesia. The level of protein extravasation under baseline conditions might have been underestimated due to direct activation of GABAA receptors by high doses of barbiturates (Owen et al. 1986).

The fact that plasma protein extravasation is completely blocked by valproate and muscimol following trigeminal stimulation, whereas leakage caused by exogenous SP is only partially blocked suggests that a fraction of the relevant GABAA receptors might be located on primary afferent fibers. Putative presynaptic GABAA heteroreceptors may reside on trigeminal nerve fibers in a manner similar to that described for the $5-HT_{1D\alpha}$ receptor subtype, which is the putative target of the antimigraine drug sumatriptan (Rebeck et al. 1994; Moskowitz, 1992).

EQUIVALENTS

Those skilled in the art will be able to ascertain, using no more than routine experimentation, many equivalents of the specific embodiments of the invention described herein.

These and all other equivalents are intended to be encompassed by the following claims.

I claim:

1. A method for treating migraine comprising administering to a subject in need of such treatment an effective amount of an agonist that binds to a benzodiazepine binding site of a $GABA_A$ receptor and is a GABAergic modulator of $GABA_A$ receptor activity.

2. The method of claim 1, wherein the agonist that binds to the benzodiazepine binding site is a benzodiazepine that binds to the $GABA_A$ receptor and modulates $GABA_A$ receptor activity.

3. The method of claim 2, wherein the benzodiazepine is FG8205.

4. The method of claim 2, wherein the benzodiazepine is bretazenil.

5. The method of claim 2, wherein the benzodiazepine is alprazolam.

6. The method of claim 2, wherein the benzodiazepine is diazepam.

7. The method of claim 2, wherein the benzodiazepine is zolpidem.

8. The method of claim 1, wherein the agonist that binds to the benzodiazepine binding site of the $GABA_A$ receptor is selected from the group consisting of clonazepam; FG8205; bretazenil (Ro166028); divaplon (RU32698); alpidem; abecarnil (ZK11219); alprazolam; diazepam; zolpidem and flunitrazepam [; Ro54864:7-chloro- 1,3-dihydro-1-methyl-5-(p-chlorophenyl) -2H-1, 4-benzodiazepine-2-one; PK8165; phenyl-2[(piperidinyl4)-2-ethyl]4-quinoline; PK0984; phenyl-2[piperidinyl-3)-2-ethyl]-4-quinoline; and PK11195:1-(2-chlorophenyl)-N-methyl-N-(1-methylpropyl)-3-isoquinalinecarboxamide].

9. The method of claim 8, wherein the agonist that binds to the benzodiazepine binding site is divaplon.

10. The method of claim 8, wherein the agonist that binds to the benzodiazepine binding site is alpidem.

11. The method of claim 8, wherein the agonist that binds to the benzodiazepine binding site is abecarnil.

12. The method of claim 8, wherein the agonist that binds to the benzodiazepine binding site is flunitrazepam.

* * * * *